United States Patent
Ikeda et al.

(10) Patent No.: US 11,525,876 B2
(45) Date of Patent: Dec. 13, 2022

(54) COUCH AND MAGNETIC RESONANCE IMAGING DEVICE

(71) Applicant: CANON MEDICAL SYSTEMS CORPORATION, Otawara (JP)

(72) Inventors: Kaoru Ikeda, Yokohama (JP); Yohei Hashizume, Ota-ku (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/119,359

(22) Filed: Dec. 11, 2020

(65) Prior Publication Data

US 2021/0199738 A1 Jul. 1, 2021

(30) Foreign Application Priority Data

Dec. 26, 2019 (JP) .............................. JP2019-235620
Nov. 10, 2020 (JP) .............................. JP2020-186947

(51) Int. Cl.
*G01R 33/30* (2006.01)
*G01R 33/34* (2006.01)

(52) U.S. Cl.
CPC ..... *G01R 33/307* (2013.01); *G01R 33/34007* (2013.01)

(58) Field of Classification Search
CPC .................. G01R 33/307; G01R 33/34007
See application file for complete search history.

(56) References Cited

U.S. PATENT DOCUMENTS

| | | | |
|---|---|---|---|
| 5,461,314 A | 10/1995 | Arakawa et al. | |
| 5,565,779 A | 10/1996 | Arakawa et al. | |
| 5,577,503 A * | 11/1996 | Bonutti | A61B 6/0421 |
| | | | 600/415 |
| 8,131,341 B2 * | 3/2012 | Heumann | G01R 33/307 |
| | | | 600/415 |
| 2007/0096739 A1 | 5/2007 | Nakabayashi | |
| 2009/0182221 A1 | 7/2009 | Kasugai | |
| 2016/0151025 A1 | 6/2016 | Gatayama et al. | |

FOREIGN PATENT DOCUMENTS

| | | |
|---|---|---|
| JP | 1-223939 A | 9/1989 |
| JP | 7-204177 A | 8/1995 |
| JP | 2009-183689 A | 8/2009 |
| JP | 2010-005321 A | 1/2010 |
| JP | 5238156 B2 | 7/2013 |
| JP | 2015-006329 A | 1/2015 |

* cited by examiner

*Primary Examiner* — G. M. A Hyder
(74) *Attorney, Agent, or Firm* — Oblon, McClelland, Maier & Neustadt, L.L.P.

(57) ABSTRACT

A couch according to an embodiment is a couch for a magnetic resonance imaging device, and includes a transformable couchtop, a movable couchtop, and processing circuitry. The transformable couchtop is configured to be at least partially transformable and to support a subject. The movable couchtop is configured to cause the transformable couchtop to move into a gantry of the magnetic resonance imaging device. The processing circuitry is configured to control transformation of the transformable couchtop. The processing circuitry is configured to acquire information regarding a receiver coil used in imaging of the subject, and to control the transformation of the transformable couchtop based on the information regarding the receiver coil.

17 Claims, 10 Drawing Sheets

COUCH AND MAGNETIC RESONANCE IMAGING DEVICE

CROSS-REFERENCE TO RELATED APPLICATIONS

This application is based upon and claims the benefit of priority from Japanese Patent Application No. 2019-235620, filed on Dec. 26, 2019, and Japanese Patent Application No. 2020-186947, filed on Nov. 10, 2020; the entire contents of which are incorporated herein by reference.

FIELD

Embodiments disclosed in the present specification with reference to the accompanying drawings relate to a couch and a magnetic resonance imaging device.

BACKGROUND

Conventionally, in imaging with a magnetic resonance imaging device, a body movement of a subject is known to lower image quality. It is thus necessary to restrict a body position of the subject from changing during imaging. In terms of subject's comfort, however, restricting a body position from changing as described above places a large burden on a subject. Therefore, to allow a subject to secure a comfortable posture during imaging, for example, such a method is used that a third party such as a technician places a cushion on a couchtop, for example. In imaging with a magnetic resonance imaging device, however, a single technician normally deals with a subject and performs imaging in many cases. Reducing a work burden on a technician has thus been demanded.

DETAILED DESCRIPTION

A couch according to an embodiment is a couch for a magnetic resonance imaging device, and includes a transformable couchtop, a movable couchtop, and a couch controller. The transformable couchtop is configured to be at least partially transformable and to support a subject. The movable couchtop is configured to cause the transformable couchtop to move into a gantry of the magnetic resonance imaging device. The couch controller is configured to control transformation of the transformable couchtop. The couch controller is configured to acquire information regarding a receiver coil used in imaging of the subject, and to control the transformation of the transformable couchtop based on the information regarding the receiver coil.

The embodiments of a couch and a magnetic resonance imaging device according to the present application will now be described in detail with reference to the accompanying drawings.

First Embodiment

Figure 1:
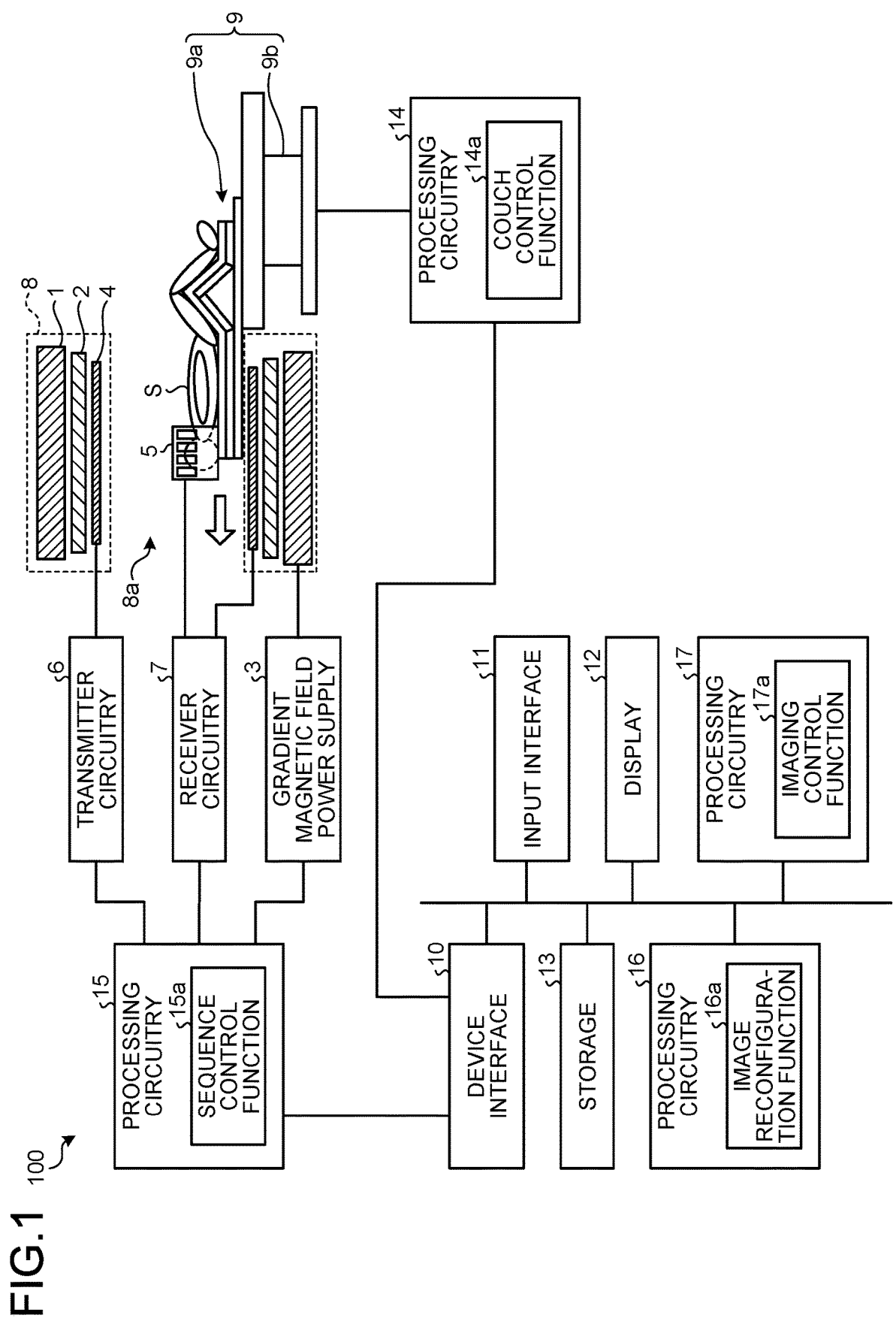
FIG. 1 is a view of an example configuration of a magnetic resonance imaging device according to a first embodiment.

FIG. 1 is a view of an example configuration of a magnetic resonance imaging (MRI) device according to a first embodiment.

For example, as illustrated in FIG. 1, an MRI device 100 includes a static magnetic field 1, a gradient coil 2, a gradient magnetic field power supply 3, a whole body (WB) coil 4, a local coil 5, transmitter circuitry 6, receiver circuitry 7, a gantry 8, a couch 9, an input interface 11, a display 12, a storage 13, and processing circuitries 14 to 17.

The static magnetic field 1 is configured to generate a static magnetic field in an imaging space in which a subject S lies. Specifically, the static magnetic field 1 is formed into a hollow, substantially cylindrical shape (including those where a cross sectional shape orthogonal to a central axis is elliptical) to generate a static magnetic field in the imaging space formed on its inner circumference side. For example, the static magnetic field 1 is a superconducting magnet or a permanent magnet. The superconducting magnet referred herein includes, for example, a vessel filled with a cooling agent such as liquid helium, and a superconducting coil immersed in the vessel.

The gradient coil 2 is disposed inside of the static magnetic field 1 to generate a gradient magnetic field in the imaging space in which the subject S lies. Specifically, the gradient coil 2 is formed into a hollow, substantially cylindrical shape (including those where a cross sectional shape orthogonal to a central axis is elliptical), and includes an X coil, a Y coil, and a Z coil respectively corresponding to an X axis, a Y axis, and a Z axis that are orthogonal to each other. The X coil, the Y coil, and the Z coil each generate, based on an electric current supplied from the gradient magnetic field power supply 3, a gradient magnetic field that changes linearly in axial directions in the imaging space. Here, the Z axis is set to extend along magnetic flux of a static magnetic field generated by the static magnetic field 1. The X axis is set to extend in a horizontal direction that is orthogonal to the Z axis. The Y axis is set to extend in a perpendicular direction that is orthogonal to the Z axis. Therefore, the X axis, the Y axis, and the Z axis configure a unique device coordinate system in the MRI device 100.

The gradient magnetic field power supply 3 is configured to supply an electric current to the gradient coil 2 to generate a gradient magnetic field in the imaging space. Specifically, the gradient magnetic field power supply 3 separately supplies an electric current to the X coil, the Y coil, and the Z coil of the gradient coil 2 to each generate a gradient magnetic field that linearly changes in a readout direction, a phase encoding direction, and a slice direction that are orthogonal to each other in the imaging space. A gradient magnetic field extending in the readout direction will be hereinafter referred to as a readout gradient magnetic field. A gradient magnetic field extending in the phase encoding direction will be hereinafter referred to as a phase encoding gradient magnetic field. A gradient magnetic field extending in the slice direction will be hereinafter referred to as a slice gradient magnetic field.

Here, the readout gradient magnetic field, the phase encoding gradient magnetic field, and the slice gradient magnetic field are each superimposed on a static magnetic field generated by the static magnetic field 1 to give spatial position information to a magnetic resonance signal generated from the subject S. Specifically, the readout gradient magnetic field causes a frequency of a magnetic resonance signal to change in accordance with a position in the readout direction to give position information in line with the readout direction to the magnetic resonance signal. The phase encoding gradient magnetic field causes a phase of a magnetic resonance signal to change in the phase encoding direction to give position information in line with the phase encoding direction to the magnetic resonance signal. The slice gradient magnetic field gives position information in line with the slice direction to a magnetic resonance signal. For example, the slice gradient magnetic field is used to determine a direction and a thickness of a slice region and the number of the slice regions, when an imaging region is a slice region (two dimensional (2D) imaging), or is used to change a phase of a magnetic resonance signal in accordance with a position in the slice direction, when an imaging region is a volume region (three dimensional (3D) imaging). Therefore, an axis extending in the readout direction, an axis extending in the phase encoding direction, and an axis extending in the slice direction configure a logical coordinate system used to define a slice region or a volume region serving as an imaging target.

The WB coil 4 is disposed on an inner circumference side of the gradient coil 2, and has a function of applying a high-frequency magnetic field to the subject S lying in the imaging space, and a function of receiving a magnetic resonance signal generated from the subject S due to the effects of the high-frequency magnetic field. Specifically, the WB coil 4 is formed into a hollow, substantially cylindrical shape (including those where a cross sectional shape orthogonal to a central axis is elliptical), and is configured to apply, based on a high-frequency pulse signal supplied from the transmitter circuitry 6, a high-frequency magnetic field to the subject S lying in the imaging space positioned on its inner circumference side. The WB coil 4 is further configured to receive a magnetic resonance signal generated from the subject S due to the effects of the high-frequency magnetic field, and to output the received magnetic resonance signal to the receiver circuitry 7.

The local coil 5 has a function of receiving a magnetic resonance signal generated from the subject S. Specifically, to apply the local coil 5 at each of different portions of the subject S, a plurality of types are prepared. To allow the subject S to undergo imaging, the local coil 5 is disposed at a position adjacent to a surface of an imaging-target portion. The local coil 5 is configured to then receive a magnetic resonance signal generated from the subject S due to the effects of a high-frequency magnetic field applied by the WB coil 4, and to output the received magnetic resonance signal to the receiver circuitry 7. The local coil 5 may further have a function of applying a high-frequency magnetic field to the subject S. In that case, the local coil 5 is connected to the transmitter circuitry 6 to apply, based on a high-frequency pulse signal supplied from the transmitter circuitry 6, a high-frequency magnetic field to the subject S. For example, the local coil 5 constitutes a surface coil, or a phased array coil including a plurality of surface coils serving as coil elements combined with each other.

The transmitter circuitry 6 is configured to output, to the WB coil 4, a high-frequency pulse signal corresponding to a Larmor frequency that is unique to a target atomic nucleus placed in a static magnetic field. Specifically, the transmitter circuitry 6 includes a pulse generator, a high-frequency generator, a modulator, and an amplifier. The pulse generator is configured to generate a waveform of a high-frequency pulse signal. The high-frequency generator is configured to generate a high-frequency signal at a resonant frequency (Larmor frequency). The modulator is configured to modulate, with the waveform generated by the pulse generator, amplitude of the high-frequency signal generated by the high-frequency generator to generate a high-frequency pulse signal. The amplifier is configured to amplify the high-frequency pulse signal generated by the modulator, and to output the amplified high-frequency pulse signal to the WB coil 4.

The receiver circuitry 7 is configured to generate magnetic resonance (MR) data based on a magnetic resonance signal output from the WB coil 4 or the local coil 5, and to output the generated MR data to the processing circuitry 15. For example, the receiver circuitry 7 includes a selector, a previous-stage amplifier, a phase detector, and an analog/digital (A/D) converter. The selector is configured to selectively input a magnetic resonance signal output from the WB coil 4 or the local coil 5. The previous-stage amplifier is configured to power-amplify the magnetic resonance signal output from the selector. The phase detector is configured to detect a phase of the magnetic resonance signal output from the previous-stage amplifier. The A/D converter is configured to convert an analog signal output from the phase detector into a digital signal to generate MR data, and to output the generated MR data to the processing circuitry 15. Here, it is not necessary that the receiver circuitry 7 necessarily wholly perform the processing that the receiver circuitry 7 is supposed to perform, as described above. The processing may partially take place in the WB coil 4 or the local coil 5 (for example, the processing that the A/D converter performs).

The gantry 8 has a hollow bore 8a formed into a substantially cylindrical shape (including those where a cross sectional shape orthogonal to a central axis is elliptical) to accommodate the static magnetic field 1, the gradient coil 2, and the WB coil 4. Specifically, the gantry 8 accommodates the WB coil 4 disposed on an outer circumference side of the bore 8a, the gradient coil 2 disposed on an outer circumference side of the WB coil 4, and the static magnetic field 1 disposed on an outer circumference side of the gradient coil 2. Here, a space in the bore 8a that the gantry 8 has serves as the imaging space in which the subject S lies during imaging.

The couch 9 includes a couchtop 9a on which the subject S lies, and a couch main body 9b supporting the couchtop 9a. Here, the couch main body 9b includes a movement mechanism configured to cause the couchtop 9a to move in upper and lower directions and the horizontal direction. The movement mechanism thus causes the couchtop 9a to move between a space outside of the gantry 8 and the imaging space in the bore 8a of the gantry 8.

Such an example case will be described in here that the MRI device 100 has a so-called, tunnel-shaped structure where the static magnetic field 1, the gradient coil 2, and the WB coil 4 are each formed into a substantially cylindrical shape. There are embodiments that are not limited by the example case, however. For example, the MRI device 100 may have a so-called, open-shaped structure where a pair of static magnetic fields, a pair of gradient coils, and a pair of radio frequency (RF) coils are disposed to face each other with respect to the imaging space in which the subject S lies. In the open-shaped structure described above, a space created by the pair of static magnetic fields, the pair of gradient coils, and the pair of RF coils corresponds to the bore in the tunnel-shaped structure.

The device interface 10 is configured to control transmitting and receiving of various kinds of signals to be exchanged among the input interface 11, the display 12, the storage 13, the processing circuitries 16 and 17, and the processing circuitries 14 and 15.

The input interface 11 is configured to accept input operations of various kinds of instructions and various kinds of information from an operator. Specifically, the input interface 11 is connected to the processing circuitry 17 to convert an input operation received from the operator into an electric signal, and to output the electric signal to the processing circuitry 17. For example, the input interface 11 is achieved, for setting imaging conditions and a region of interest (ROI) and for performing other operations, by a trackball, switch buttons, a mouse, a keyboard, a touch pad having an operation face to be touched for an input operation, a touch screen in which a display screen and a touch pad are integrated with each other, a non-contact input circuit using an optical sensor, and a voice input circuit, for example. In the present specification, the input interface 11 is not limited to those that include physical operation parts such as a mouse and a keyboard. For example, examples of the input interface 11 include processing circuitry for electric signals. The processing circuitry is configured to receive an electric signal corresponding to an input operation, from an external input device provided separately from the present device, and to output the electric signal to control circuitry.

The display 12 is configured to display various kinds of information and various kinds of images. Specifically, the display 12 is connected to the processing circuitry 17 to accept, from the processing circuitry 17, and convert transmitted data of various kinds of information and various kinds of images into an electric signal, and to output the electric signal. For example, the display 12 is achieved by, for example, a liquid crystal monitor or a cathode ray tube (CRT) monitor, and a touch panel.

The storage 13 is configured to store various kinds of data and various kinds of computer programs. Specifically, the storage 13 is connected to the processing circuitries 14 to 17 to store various kinds of data and various kinds of computer programs that the respective processing circuitries input and output. For example, the storage 13 is achieved by, for example, a semiconductor memory element, such as a random access memory (RAM) or a flash memory, or a hard disc or an optical disc.

The processing circuitry 14 has a couch control function 14a. The couch control function 14a is configured to output a control electric signal to the couch 9 to control the couch 9 for its operation. For example, the couch control function 14a accepts, via the input interface 11 or an operation panel provided on the gantry 8, an instruction, from the operator, of causing the couchtop 9a to move in the upper and lower directions or left and right directions. The couch control function 14a then follows the instruction accepted from the operator to cause the movement mechanism that the couch main body 9b includes to cause the couchtop 9a to operate. For example, the couch control function 14a causes, to allow the subject S to undergo imaging, the couchtop 9a on which the subject S lies to move into the imaging space in the bore 8a of the gantry 8.

The processing circuitry 15 has a sequence control function 15a. The sequence control function 15a is configured to execute various kinds of pulse sequences to collect MR data of the subject S. Specifically, the sequence control function 15a follows sequence execution data output from the processing circuitry 17 to drive the gradient magnetic field power supply 3, the transmitter circuitry 6, and the receiver circuitry 7 to execute various kinds of pulse sequences. Here, the sequence execution data is data representing a pulse sequence, or information defining, for example, a timing at which the gradient magnetic field power supply 3 supplies an electric current to the gradient coil 2 and strength of the electric current to be supplied, a timing at which the transmitter circuitry 6 supplies a high-frequency pulse signal to the WB coil 4 and strength of a high-frequency pulse to be supplied, and a timing at which the receiver circuitry 7 samples a magnetic resonance signal. The sequence control function 15a then receives MR data output from the receiver circuitry 7 as a result of execution of a pulse sequence, and causes the storage 13 to store the MR data. At this time, the MR data to be stored in the storage 13 is given, by the readout gradient magnetic field, the phase encoding gradient magnetic field, and the slice gradient magnetic field described above, position information in line with directions including the readout direction, a phase-out direction, and the slice direction, and stored as k space data representing a two-dimensional or three-dimensional k space.

The processing circuitry 16 has an image reconfiguration function 16a. The image reconfiguration function 16a is configured to generate various kinds of images based on the MR data collected by the sequence control function 15a. Specifically, the image reconfiguration function 16a reads from the storage 13 the MR data collected by the sequence control function 15a, and allows the read MR data to undergo reconfiguration processing such as Fourier transformation to generate a two-dimensional or three-dimensional image. The image reconfiguration function 16a then causes the storage 13 to store the generated image. The processing circuitry 16 may be embedded in the couch main body 9b, or may be independent from the couch 9.

The processing circuitry 17 controls the components that the MRI device 100 includes to control the whole MRI device 100. Specifically, the processing circuitry 17 causes the display 12 to display a graphical user interface (GUI) to accept an input operation regarding various kinds of instructions and various kinds of information from the operator, and follows the input operation accepted via the input interface 11 to control the components that the MRI device 100 includes. The processing circuitry 17 has an imaging control function 17a. The imaging control function 17a is configured to execute imaging of the subject S based on imaging conditions entered by the operator. Specifically, the imaging control function 17a generates sequence execution data based on the imaging conditions, and outputs the generated sequence execution data to the sequence control function 15a of the processing circuitry 15 to cause the sequence control function 15a to collect MR data. The imaging control function 17a then controls and causes the image reconfiguration function 16a of the processing circuitry 16 to reconfigure an image based on the MR data collected by the sequence control function 15a.

The example configuration of the MRI device 100 according to the present embodiment has been described above. Under such a configuration as described above, the MRI device 100 according to the present embodiment allows the subject S lying on the couchtop 9a of the couch 9 in the bore 8a of the gantry 8 to undergo imaging.

Here, in imaging with an MRI device, a body movement of a subject is generally known to lower image quality. It is thus necessary to restrict a body position of the subject from changing during imaging. In terms of subject's comfort, however, restricting a body position from changing as described above places a large burden on a subject. Therefore, to allow a subject to secure a comfortable posture during imaging, for example, such a method is used that a third party such as a technician places a cushion on a couchtop, for example. In imaging with an MRI device, however, a single technician normally deals with a subject and performs imaging in many cases. Reducing a work burden on a technician has thus been demanded.

To this end, the MRI device 100 according to the present embodiment is configured to reduce a burden on a subject and a technician, for example, involving suppression of body movements of the subject.

Specifically, in the present embodiment, the couch 9 included in the MRI device 100 includes a transformable couchtop configured to be at least partially transformable and to support the subject S, and a movable couchtop configured to cause the transformable couchtop to move into the gantry 8 in the MRI device 100. The couch control function 14a of the processing circuitry 14 then controls transformation of the transformable couchtop. Here, the couch control function 14a acquires information regarding a receiver coil used in imaging of the subject S, and controls, based on the information regarding the receiver coil, transformation of the transformable couchtop. The couch control function 14a is an example of a couch controller.

According to such a configuration as described above, controlling transformation of the transformable couchtop in accordance with the receiver coil used in imaging makes it possible to restrict the transformable couchtop from being transformed at a position adjacent to an imaging-target portion, which may affect image quality, or to allow the transformable couchtop to be transformed at a part which does not affect image quality to allow the subject S to secure a comfortable posture, for example. Therefore, according to the present embodiment, it is possible to reduce a burden on a subject and a technician, for example, involving suppression of body movements of the subject.

The configuration of the couch 9 will now be described in detail. Such an example case is described below that the local coil 5 is used as a receiver coil.

In the example case described below, the MRI device 100 includes, as an example transformable couchtop, a bendable couchtop configured to be at least partially bendable, and the couch control function 14a controls bending of the bendable couchtop, as an example of controlling transformation of the transformable couchtop. That is, transformation in the present embodiment includes bending. More specifically, in the example case described below, the couch control function 14a restricts the bendable couchtop from bending, as an example of controlling bending of the bendable couchtop.

In the example case described below, as information regarding the receiver coil, type information and position information of the receiver coil are used.

Figure 2:
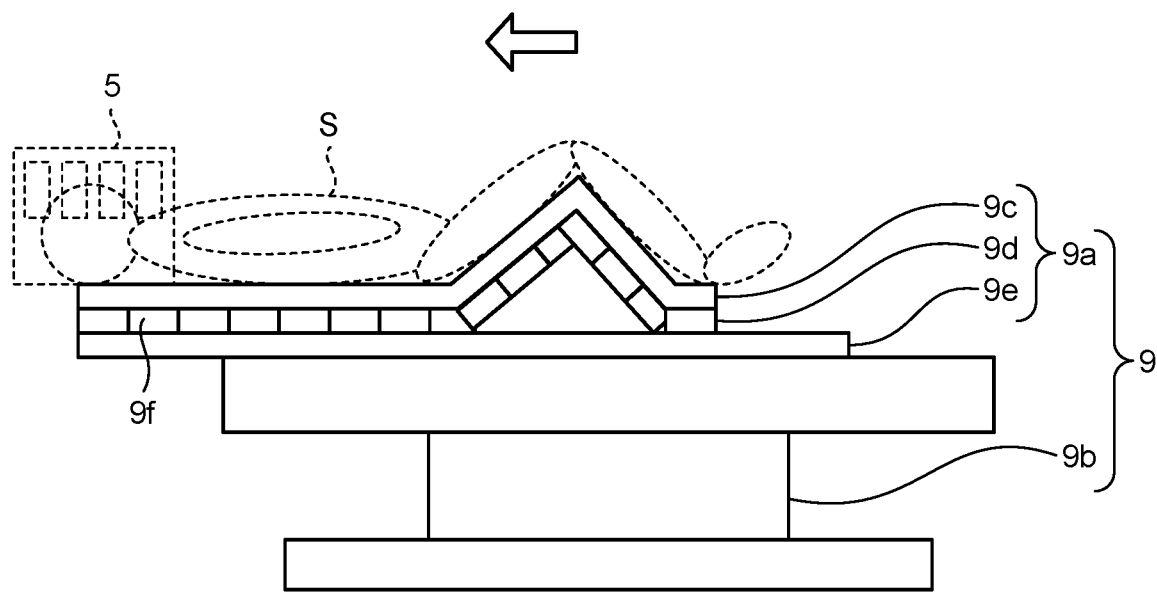
FIG. 2 is a view of an example configuration of a couch according to the first embodiment.
Figure 3:
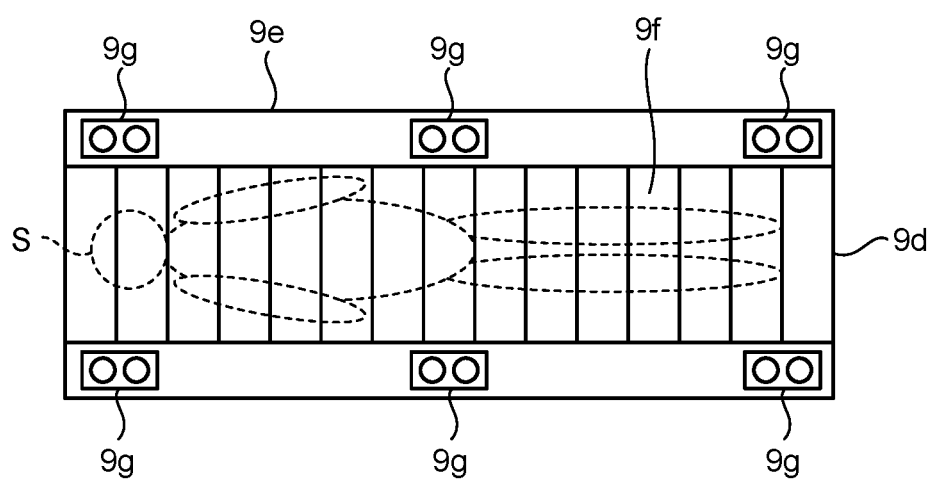
FIG. 3 is a view of an example configuration of the couch according to the first embodiment.

FIGS. 2 and 3 are views of example configurations of the couch 9 according to the first embodiment.

For example, as illustrated in FIG. 2, the couch 9 includes the couchtop 9a on which the subject S lies, and the couch main body 9b supporting the couchtop 9a.

The couchtop 9a includes a couchtop mat 9c, a bendable couchtop 9d, and a movable couchtop 9e.

The couchtop mat 9c is a mat covering an upper surface of the bendable couchtop 9d. Specifically, the couchtop mat 9c is a plate member made of a flexible material, and, as the bendable couchtop 9d bends, is transformed in accordance with a shape of the bendable couchtop 9d.

The bendable couchtop 9d is configured to be at least partially bendable to support the subject S. Specifically, the bendable couchtop 9d is formed by coupling a plurality of plate members 9f with bendable coupling members such as hinges, and is configured to cause the coupling members to bend at desired angles to form a desired shape.

The movable couchtop 9e is configured to cause the bendable couchtop 9d to move into the gantry 8 of the MRI device 100. Specifically, the movable couchtop 9e is disposed on an upper surface of the couch main body 9b to support, with its upper surface, the bendable couchtop 9d in a bendable manner. The movable couchtop 9e then moves in a direction toward or away from the gantry 8 to cause the bendable couchtop 9d to move into the gantry 8.

The couch main body 9b includes the bendable couchtop 9d and the movable couchtop 9e. Specifically, the couch main body 9b has the movable couchtop 9e slidably mounted on the upper surface of the couch main body 9b, and causes, with the movement mechanism described above, the movable couchtop 9e to move in the direction toward or away from the gantry 8.

The couch 9 has a plurality of coil ports used to connect the local coil 5.

For example, as illustrated in FIG. 3, coil ports 9g are provided at six locations on the movable couchtop 9e. Specifically, in a longer direction of the movable couchtop 9e, an end portion on a side proximal to the gantry 8, a central portion, and an end portion on a side distal from the gantry 8 are each provided with two of the coil ports 9g.

Here, to allow the subject S to undergo imaging, a technician connects, after making sure that the subject S lies on the couchtop 9a, the local coil 5 for an imaging-target portion to one coil port 9g that lies at a position adjacent to the imaging-target portion, among the coil ports 9g. At this time, the local coil 5 is connected directly or via a cable to the one of the coil ports 9g, and is fixed at a position adjacent to the imaging-target portion on the couchtop 9a. The local coil 5 is connected, after connected to the one of the coil ports 9g, to the couch main body 9b via the one of the coil ports 9g, and further connected to the receiver circuitry 7 via a cable arranged in the couch main body 9b.

In the present embodiment, the couch control function 14a of the processing circuitry 14 then acquires, after the local coil 5 used in imaging is connected to the movable couchtop 9e, type information and position information of the local coil 5, and, based on the type information and the position information, sets a bending restricted region for the bendable couchtop 9d. Here, the bending restricted region is an example of a transformation controlled region.

Specifically, the couch control function 14a acquires, as the type information, a coil length of the local coil 5 and information indicating the imaging-target portion representing of the local coil 5. For example, the couch control function 14a reads, after the local coil 5 is connected to the one of the coil ports 9g on the movable couchtop 9e, a coil ID from the local coil 5 via the one of the coil ports 9g. The couch control function 14a then refers to a table, which is stored beforehand in the storage 13, and in which the coil ID and information regarding the coil, such as a type and the number of channels of the local coil 5, are associated with each other, so as to acquire the coil length associated with the read coil ID and the information indicating the imaging-target portion, as the type information regarding the local coil 5. The couch control function 14a acquires information indicating a position of the one of the coil ports 9g, which is connected with the local coil 5, as the position information of the local coil 5.

After that, the couch control function 14a sets, based on the acquired type information and the acquired position information, a bending restricted region for the bendable couchtop 9d.

Here, for example, the bending restricted region is determined based on a ratio with respect to the coil length of the local coil 5. For example, the ratio referred herein with respect to the coil length is 1.0 or greater.

Specifically, the couch control function 14a sets, as the bending restricted region, a range within which additional regions are added, in an advancing direction of the bendable couchtop 9d, at positions in front of and behind a region determined based on the coil length of the local coil 5.

Figure 4:
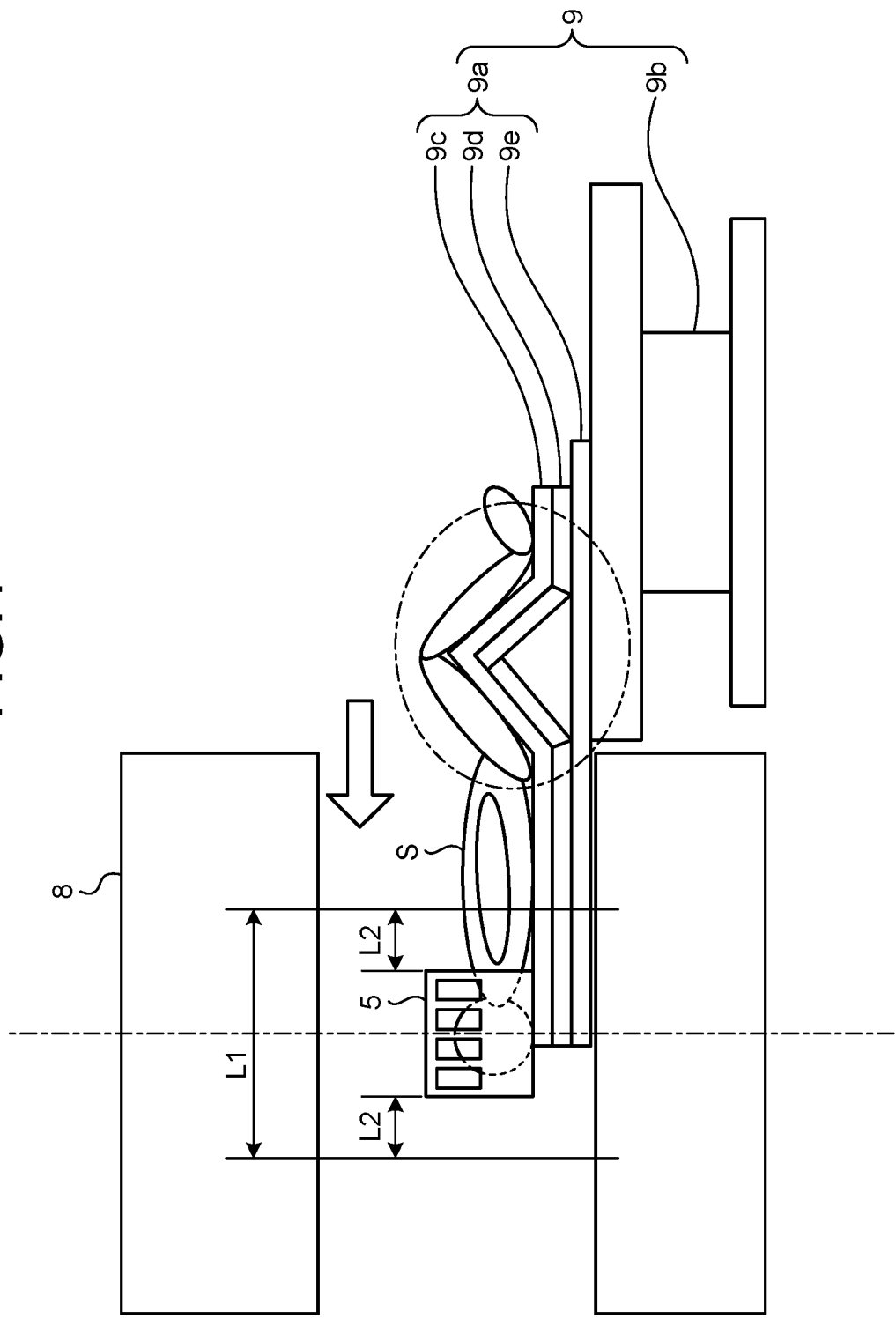
FIG. 4 is a view of an example of how a couch control function according to the first embodiment sets a transformation controlled region.
Figure 5:
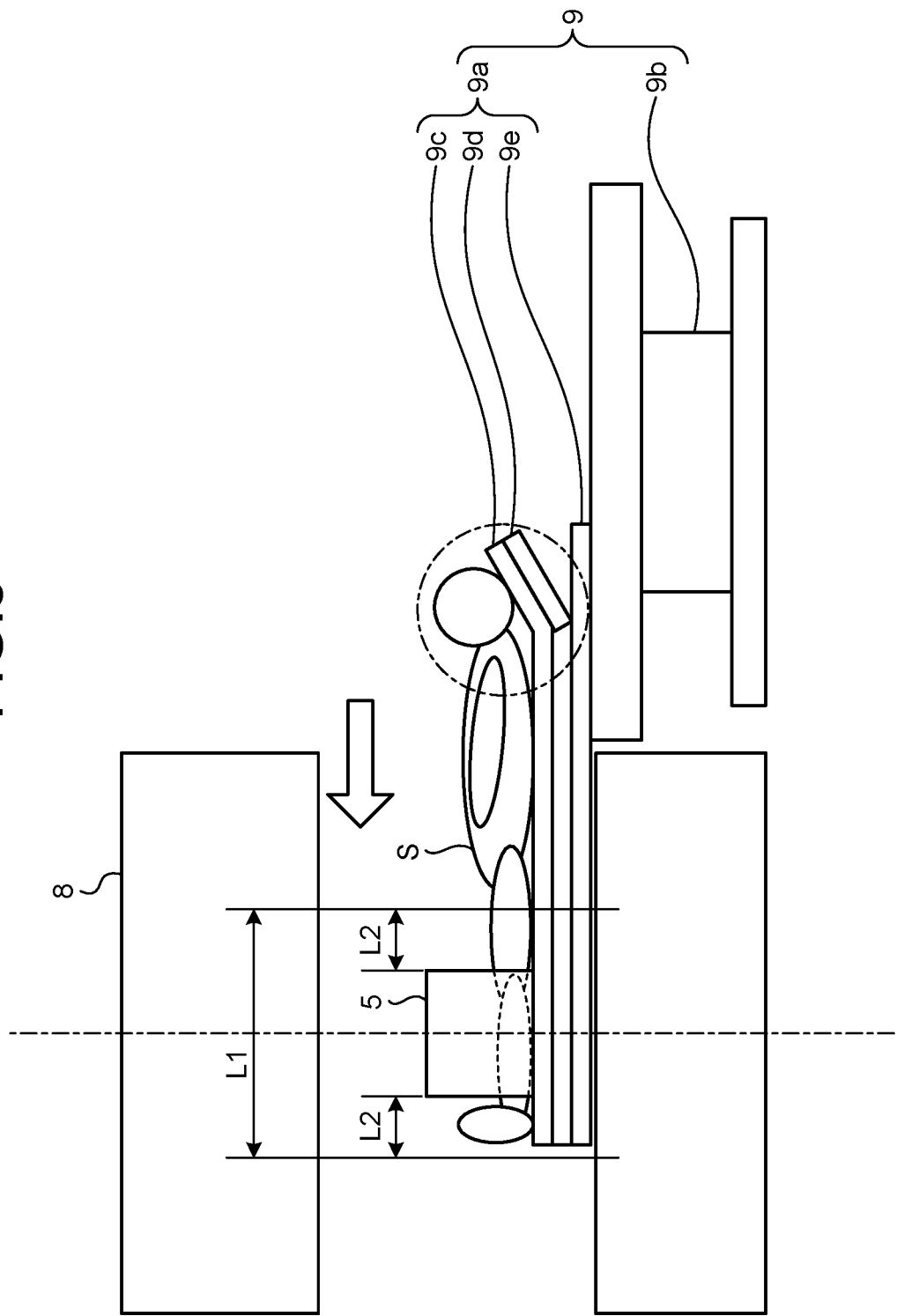
FIG. 5 is a view of an example of how the couch control function according to the first embodiment sets a transformation controlled region.

FIGS. 4 and 5 are views of examples of how the couch control function 14a according to the first embodiment sets a transformation controlled region.

For example, as illustrated in FIG. 4, when an imaging-target portion of the subject S is the head, the couch control function 14a sets, as a bending restricted region L1, a range within which additional regions L2 are added at positions in front of and behind a region having a size identical to the coil length of the local coil 5 for head.

For example, as illustrated in FIG. 5, when an imaging-target portion of the subject S is the legs, the couch control function 14a sets, as the bending restricted region L1, a range within which the additional regions L2 are added at positions in front of and behind a region having a size identical to the coil length of the local coil 5 for legs.

At this time, the couch control function 14a sets the additional regions L2 to allow a ratio of the bending restricted region L1 with respect to the coil length of the local coil 5 to be a predetermined value that is 1.0 or greater.

For example, as illustrated in FIGS. 4 and 5, to perform imaging, a central part of the local coil 5 is disposed at the center of a magnetic field on the gantry 8 (a position illustrated by an alternate long and short dash line in FIGS. 4 and 5). Therefore, as described above, as the couch control function 14a sets, as a bending restricted region, a range within which additional regions are added at positions in front of and behind a region having a size identical to the coil length of the local coil 5, it is possible to restrict the bendable couchtop from bending at a position adjacent to an imaging-target portion, which may affect image quality, and to suppress image quality from lowering due to a body movement of the subject S.

The method of setting the bending restricted region L1 and the additional regions L2 is not limited to the example described above.

For example, the couch control function 14a may set the additional regions L2 having sizes that the operator has desired and designated, or may set the additional regions L2 having sizes that differ depending on an imaging-target portion. The couch control function 14a may add only one of the additional regions L2 at a position either in front of or behind the local coil 5, or may set the additional regions L2 having sizes each corresponding to zero.

For example, the couch control function 14a may set the additional regions L2 having sizes that are each identical to a distance from an end of the local coil 5 to an end portion of the gantry 8 when the central part of the local coil 5 is disposed at the center of a magnetic field on the gantry 8. In this case, a bending restricted region has a size equivalent to a size of the whole interior of the gantry 8.

For example, the couch control function 14a may set the additional regions L2 based on patient information regarding the subject S, including gender, age, race, disease information, an imaging-target portion, and contraindication information, for example. In this case, for example, the couch control function 14a acquires the patient information from a hospital information system (HIS), a radiology information system (RIS), or information entered by the operator before imaging, for example. For example, the couch control function 14a then sets the additional regions L2 having sizes that differ depending on gender, age, race, and other factors of the subject S. At this time, for example, the couch control function 14a refers to a table, which is stored beforehand in the storage 13, and in which patient information and the sizes of the additional regions L2 are associated with each other, so as to acquire and set the additional regions L2 having the corresponding sizes. For example, the couch control function 14a sets, if the subject S is determined to have claustrophobia based on contraindication information, the additional regions L2 having smaller sizes, compared with a case where the subject S is determined not to have claustrophobia, so as to moderate restrictions to movements of the subject S. For example, the couch control function 14a sets, if the subject S is determined to be suffered from a disease greatly associated with coughs based on disease information, the additional regions L2 without including the upper body of the subject S.

For example, the couch control function 14a may acquire, as position information of the local coil 5, a range within which the local coil 5 is allowed to be disposed. In this case, for example, the couch control function 14a may acquire a range within which the local coil 5 is allowed to be disposed based on a cable length of a cable attached to the local coil 5.

For example, the couch control function 14a may set, when the local coil 5 is such a type that the local coil 5 is not fixed onto the couchtop 9a, but is connected to one of the coil ports 9g via a cable, the additional regions L2 having sizes determined based on a range within which the local coil 5 is allowed to be disposed. In this case, for example, the couch control function 14a acquires, when the local coil 5 is connected to one of the coil ports 9g, a cable length of a cable attached to the local coil 5. The couch control function 14a then derives a range within which the local coil 5 is allowed to be disposed based on the acquired cable length, and sets the additional regions L2 having sizes allowing the derived range to be included within the bending restricted region L1.

For example, the couch control function 14a may use a learned model constructed through machine learning using, as learning data, a disposed position of the local coil 5 in a past examination to estimate a range within which the local coil 5 is allowed to be disposed. In this case, for example, the learned model is generated based on patient information regarding a plurality of subjects, and through machine learning using, as learning data, disposed positions of the local coil 5 when the subjects underwent examinations. For example, the couch control function 14a then acquires a position of the local coil 5, which is output from the learned model as patient information regarding a target subject is entered to estimate a range within which the local coil 5 is allowed to be disposed.

Furthermore, for example, the couch control function 14a may set a bending restricted region expanding in not only the advancing direction of the bendable couchtop 9d, but also the upper and lower directions. In this case, for example, the couch control function 14a sets a bending restricted region within a range not exceeding a position that is lowered from the highest position of an inner wall of the bore 8a for the thickness of the subject S.

After the bending restricted region has been set as described above, the couch control function 14a accepts, from the operator, an instruction of causing the bendable couchtop 9d to bend into a desired shape. Here, the operator providing an instruction of causing the bendable couchtop 9d to bend may be the technician or the subject S.

For example, the couch control function 14a accepts, from the operator, an instruction of causing the bendable couchtop 9d to bend via an input device including buttons, a switch box, a touch panel, a microphone configured to receive sound including voice, and an input unit configured to accept a certain gesture, which are connected to the couch main body 9b, for example.

Here, for example, when the subject S provides an instruction of causing the bendable couchtop 9d to bend, the input device configured to accept an instruction preferably does not enter the gantry 8. Therefore, for example, the input device may be configured to allow, when the input device has been connected to the couch main body 9b with a wire, a wire part to be wound at a position distant from the gantry 8 on the couch main body 9b after the subject S has completed providing the instruction.

The couch control function 14a then follows the instruction accepted from the operator to cause the bendable couchtop 9d to bend.

For example, as illustrated in FIG. 4, when an imaging-target portion of the subject S is the head, the couch control function 14a causes a range on the bendable couchtop 9d, where the knees of the subject S lie, to bend into an upward angled shape to allow the subject S to bend the lower body to take a comfortable posture (see the location surrounded by the alternate long and short dash line illustrated in FIG. 4).

For example, as illustrated in FIG. 5, when an imaging-target portion of the subject S is the legs, the couch control function 14a causes a range on the bendable couchtop 9d, where the head of the subject S lies, to bend into an inclined shape to allow the subject S to bend the upper body to take a comfortable posture (see the location surrounded by the alternate long and short dash line illustrated in FIG. 5).

A shape into which the bendable couchtop 9d is caused to bend is not limited to the examples illustrated in FIGS. 4 and 5. For example, the couch control function 14a follows an instruction from the operator to make it possible to cause the bendable couchtop 9d to bend into one of various kinds of shapes within a range excluding a bending restricted region.

FIGS. 6A to 6G are views of example transform shapes of the transformable couchtop according to the first embodiment.

Figure 6E:
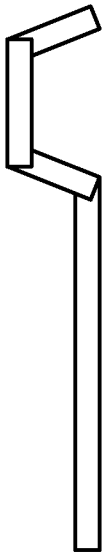
FIGS. 6A to 6G are views of example transform shapes of a transformable couchtop according to the first embodiment.
Figure 6F:
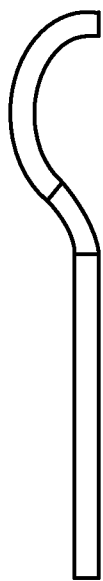
Figure 6G:
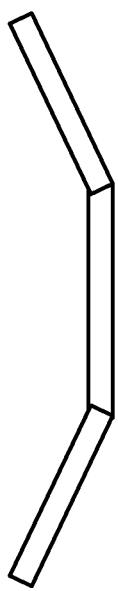
Figure 6A:
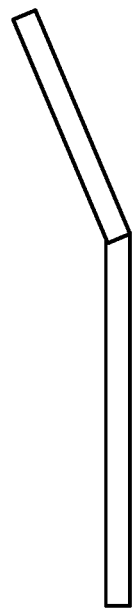
Figure 6B:
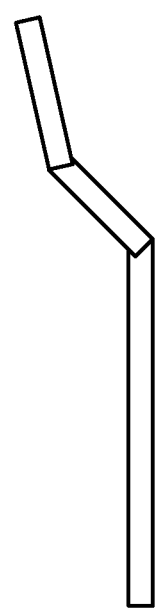
Figure 6C:
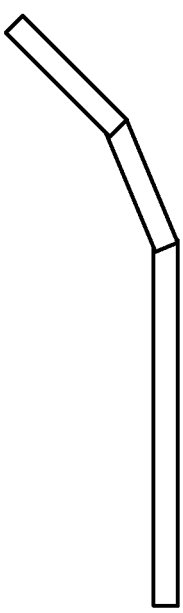

For example, the couch control function 14a may cause the bendable couchtop 9d to bend into a shape where one end portion in the longer direction is only inclined, as illustrated in FIG. 6A, or may cause the bendable couchtop 9d to bend to allow an angle of an inclined part to change at a middle position, as illustrated in FIGS. 6B and 6C.

Figure 6D:
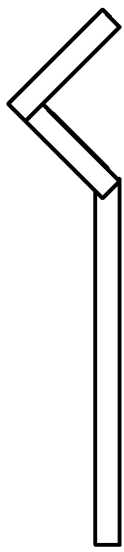

For example, the couch control function 14a may cause the bendable couchtop 9d to bend into a shape where the one end portion in the longer direction takes an upward angled shape, as illustrated in FIG. 6D, or may cause the bendable couchtop 9d to bend to allow the peak of an upward angled shape to take a trapezoidal shape, as illustrated in FIG. 6E.

For example, the couch control function 14a may cause the bendable couchtop 9d to bend to allow a bent part to be rounded, as illustrated in FIG. 6F, or may cause the bendable couchtop 9d to bend to allow both end portions in the longer direction each to have an inclined shape, as illustrated in FIG. 6G.

A position at which the bendable couchtop 9d is caused to bend is also not limited to the examples illustrated in FIGS. 4 and 5. For example, the couch control function 14a follows an instruction from the operator to make it possible to cause the bendable couchtop 9d to bend at various positions within a range excluding a bending restricted region.

Figure 7A:
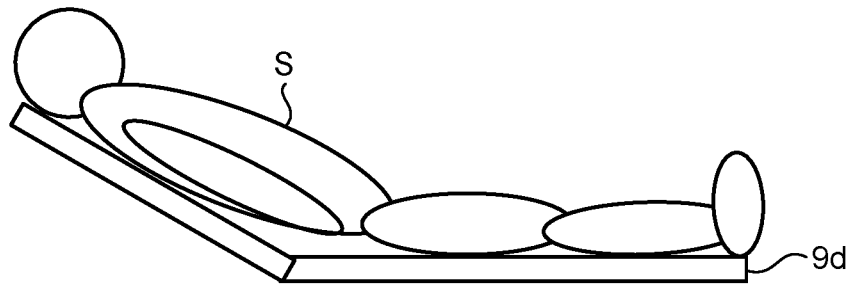
FIGS. 7A to 7C are views of example transform positions on the transformable couchtop according to the first embodiment.
Figure 7B:
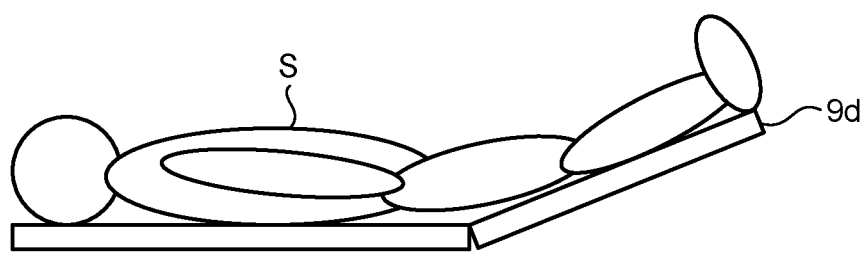
Figure 7C:
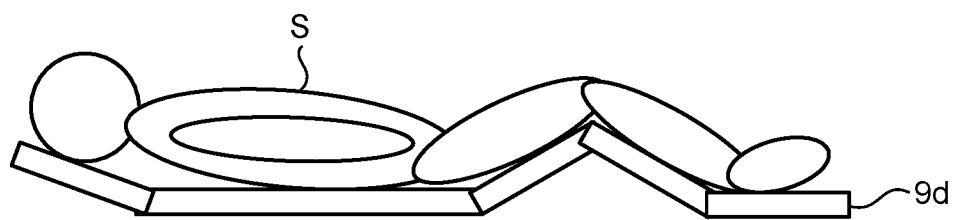

FIGS. 7A to 7C are views of example transform positions on the transformable couchtop according to the first embodiment.

For example, the couch control function 14a may cause a range on the bendable couchtop 9d, where the head and the torso of the subject S lie, to bend into an inclined shape, as illustrated in FIG. 7A. For example, the couch control function 14a may cause a range on the bendable couchtop 9d, where the whole legs of the subject S lie, to bend into an inclined shape, as illustrated in FIG. 7B.

For example, the couch control function 14a may cause a range on the bendable couchtop 9d, where the head of the subject S lies, to bend into an inclined shape, may cause a range, where the knees lie, to bend into an upward angled shape, and further, may cause a range, where the feet lie, to bend into an inclined shape, as illustrated in FIG. 7C.

As described above, as the couch control function 14a follows an instruction from the operator to cause the bendable couchtop 9d to bend into one of various kinds of shapes within a range excluding a bending restricted region, the subject S is allowed to secure a comfortable posture without using a cushion, for example.

The couch control function 14a controls, when a bending restricted region extending in the upper and lower directions is set, as described above, bending of the bendable couchtop 9d so that a height at the highest point of the bendable couchtop 9d will not exceed the bending restricted region L1 in the case of bending the bendable couchtop 9d. Therefore, even when the couchtop 9a moves into the bore 8a of the gantry 8, it is possible to prevent the subject S from coming into contact with an opening or the inner wall of the bore 8a.

The couch control function 14a may follow, when causing the bendable couchtop 9d to bend, an instruction from the operator to change a speed at which the bendable couchtop 9d is caused to bend. For example, the couch control function 14a decreases, upon the acceptance of an instruction of fine-adjusting an angle at which the bendable couchtop 9d is caused to bend, a speed at which the bendable couchtop 9d is caused to bend, and increases, upon the acceptance of an instruction of roughly adjusting an angle at which the bendable couchtop 9d is caused to bend, the speed at which the bendable couchtop 9d is caused to bend. For example, the couch control function 14a decreases, when the operator has pressed down a button for a time shorter than a predetermined time, the speed at which the bendable couchtop 9d is caused to bend, and increases, when the operator has pressed down the button for a time longer than the predetermined time, the speed at which the bendable couchtop 9d is caused to bend. For example, the couch control function 14a decreases, while the operator keeps pressing down the button, the speed at which the bendable couchtop 9d is caused to bend until a predetermined time has elapsed, and increases, after the predetermined time has elapsed, the speed at which the bendable couchtop 9d is caused to bend.

After bending of the bendable couchtop 9d has been completed by the operator, the couch control function 14a then causes the couchtop 9a on which the subject S lies to move into the bore 8a of the gantry 8.

Here, the couch control function 14a determines, upon the satisfaction of predetermined end conditions, that the bending of the bendable couchtop 9d has been completed by the operator. For example, the couch control function 14a determines, when no instruction of causing the bendable couchtop 9d to bend is accepted from the operator for a predetermined period, that the bending of the bendable couchtop 9d has been completed. For example, the couch control function 14a may be configured to explicitly accept, from the operator, an operation indicating that the bending of the bendable couchtop 9d has been completed, and may determine, upon the acceptance of the operation, that the bending of the bendable couchtop 9d has been completed. Furthermore, the couch control function 14a may determine that the bending of the bendable couchtop 9d has been completed at the time when the wire part has been wound, in such a configuration in which, when an input device configured to accept, from the operator, an instruction of causing the bendable couchtop 9d to bend has accepted such an instruction, a wire part is automatically wound by the couch main body 9b after the accepting the instruction has been completed.

The couch control function 14a then causes, when it is determined that the bending of the bendable couchtop 9d has been completed as desired by the operator, the couchtop 9a on which the subject S lies to move into the bore 8a of the gantry 8, upon the acceptance of an instruction from the operator, or automatically. The couch control function 14a may control and prohibit, as long as it is determined that the bending of the bendable couchtop 9d has not yet been completed as desired, the couchtop 9a from moving.

The configurations of the MRI device 100 and the couch 9 according to the present embodiment have been described. Here, for example, the processing circuitries 14 to 17 described above are achieved by a processor. In this case, processing functions that the respective processing circuitries have are stored in the storage 13, in the form of computer programs that are executable by a computer, for example. The respective processing circuitries then read, from the storage 13, and execute the computer programs to achieve the processing functions corresponding to the computer programs. In other words, the respective processing circuitries that have read the computer programs possess the functions indicated in the respective processing circuitries in FIG. 1.

In here, it has been described that each of the processing circuitries is achieved by a single processor. There are embodiments that are not limited by those described above, however. A plurality of independent processors may be combined to configure the respective processing circuitries. The processing functions may then be achieved as the processors execute the computer programs. The processing functions that the respective processing circuitries have may be achieved appropriately in an integrated manner into single processing circuitry or in a dispersed manner among a plurality of portions of processing circuitry. In the example illustrated in FIG. 1, it has been described that the storage 13 solely stores the computer programs corresponding to the processing functions. Such a configuration may be applied that a plurality of storages are disposed in a dispersed manner, however, and processing circuitry separately reads from the storages of the corresponding computer programs.

A processing flow to be performed by the processing functions described above will now be described.

Figure 8:
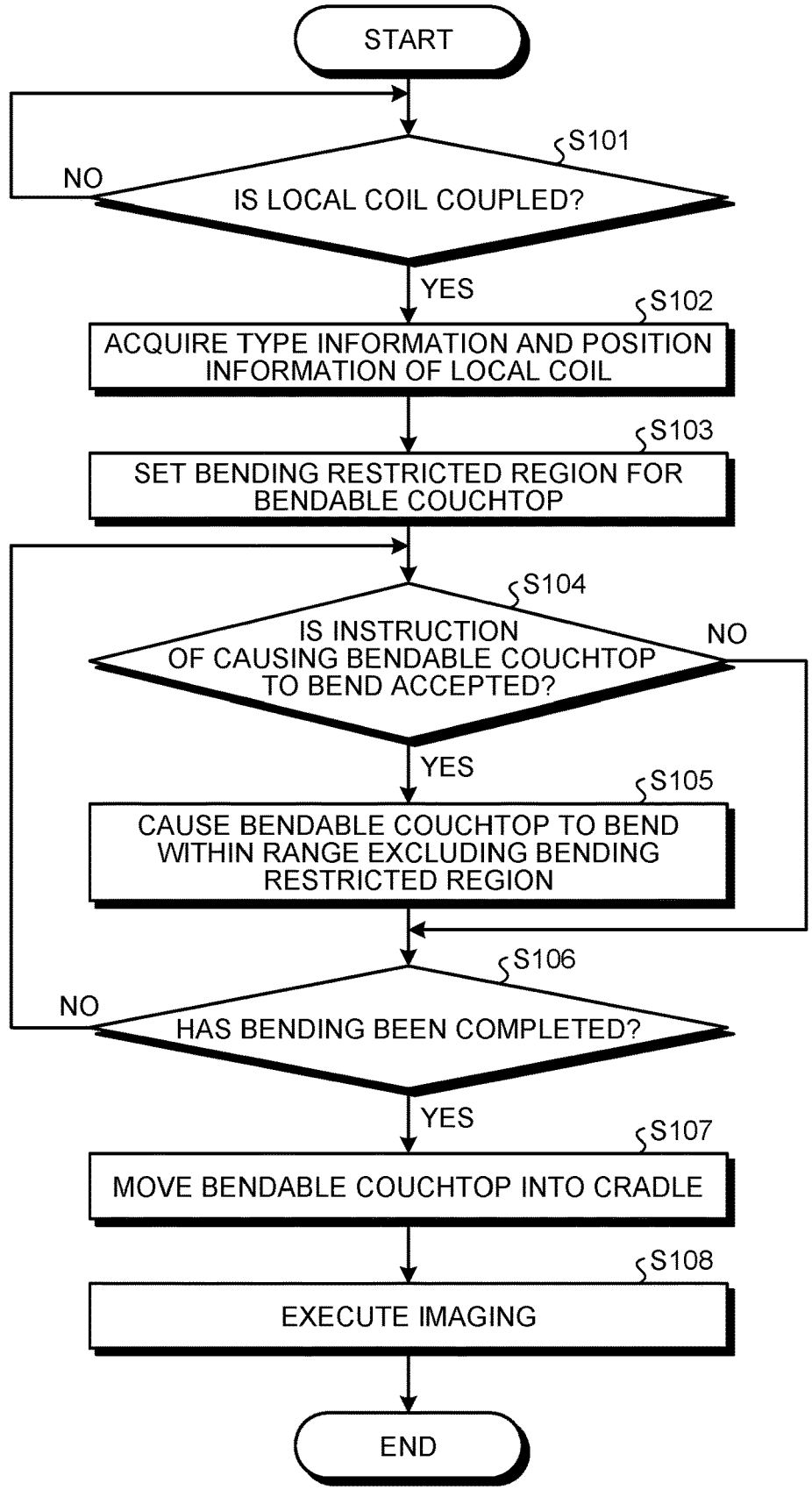
FIG. 8 is a flowchart of a processing flow to be performed by processing functions of the magnetic resonance imaging device according to the first embodiment.

FIG. 8 is a flowchart of a processing flow to be performed by the processing functions of the MRI device 100 according to the first embodiment.

For example, as the local coil 5 used in imaging is connected to the couchtop 9a via one of the coil ports 9g in the present embodiment, as illustrated in FIG. 8 (Yes at step S101), the couch control function 14a acquires type information and position information of the local coil 5 (step S102).

Next, the couch control function 14a sets, based on the acquired type information and the acquired position information, a bending restricted region for the bendable couchtop 9d (step S103).

After that, the couch control function 14a follows, upon the acceptance, from the operator, of an instruction of causing the bendable couchtop 9d to bend into a desired shape (Yes at step S104), the instruction to cause the bendable couchtop 9d to bend within a range excluding the bending restricted region (step S105).

Here, the couch control function 14a continuously accepts, until it is determined that the bending of the bendable couchtop 9d has been completed by the operator (No at step S106), the instruction from the operator, and causes the bendable couchtop 9d to bend in accordance with the accepted operation.

The couch control function 14a then causes, when it is determined that the bending of the bendable couchtop 9d has been completed by the operator (Yes at step S106), the couchtop 9a on which the subject S lied to move into the bore 8a of the gantry 8 (step S107).

After that, the imaging control function 17a executes imaging of the subject S (step S108).

Here, for example, the pieces of processing at steps S101 to S107 is achieved, for example, when the processing circuitry 17 reads, from the storage 13, and executes one computer program that corresponds to the couch control function 14a, among the computer programs. The processing at step S108 is achieved, for example, when the processing circuitry 17 reads, from the storage 13, and executes one computer program that corresponds to the imaging control function 17a, among the computer programs.

As described above, in the first embodiment, the couch 9 for the MRI device 100 includes the bendable couchtop 9d and the movable couchtop 9e. Here, the bendable couchtop 9d is configured to be at least partially bendable to support the subject S. The movable couchtop 9e is configured to cause the bendable couchtop 9d to move into the gantry 8 of the MRI device 100. The couch control function 14a of the processing circuitry 14 is configured to control bending of the bendable couchtop 9d. The couch control function 14a then acquires type information and position information of the local coil 5 used in imaging of the subject S, and, based on the type information and the position information, sets, for the bendable couchtop 9d, a bending restricted region within which bending is restricted.

According to such a configuration as described above, setting a bending restricted region based on the local coil 5 used in imaging makes it possible to restrict the bendable couchtop from bending at a position adjacent to an imaging-target portion, which may affect image quality, and to suppress image quality from lowering due to a body movement of the subject S. Furthermore, on the other hand, causing the bendable couchtop to bend within a range excluding the bending restricted region allows the subject S to secure a comfortable posture without using a cushion, for example. Therefore, according to the first embodiment, it is possible to reduce a burden on a subject and a technician, for example, involving suppression of body movements of the subject.

According to the first embodiment, setting a bending restricted region and causing the bendable couchtop 9d to bend allows the subject S to secure a comfortable posture within a region excluding the region that may affect imaging. The subject S is thus possible to keep a body position even for a longer MRI imaging time such as ten minutes or longer. Therefore, it is possible to suppress body movements of a subject during imaging, improving image quality of an image to be imaged.

The first embodiment has been described above. It is possible that the embodiment described above be implemented in such a manner that the components that the MRI device 100 includes are partially and appropriately modified. Modified examples related to the first embodiment will now be described as other embodiments. Differences from the first embodiment will be focused on and described below. Descriptions of those that are common to the first embodiment will thus be omitted.

Second Embodiment

For example, in the first embodiment described above, the example case has been described where the couch control function 14a accepts, via the input device including buttons and a switch box, for example, from the operator, an instruction of causing the bendable couchtop 9d to bend. There are embodiments that are not limited by the example case, however. For example, the couch control function 14a may accept an instruction from the operator via a graphical user interface (GUI). Such an example case will now be described as a second embodiment.

For example, the couch control function 14a presents, to the operator, information indicating a range of a bending restricted region set for the bendable couchtop 9d, and accepts, from the operator, an instruction of causing the bendable couchtop 9d to bend within a range excluding the bending restricted region.

Figure 9:
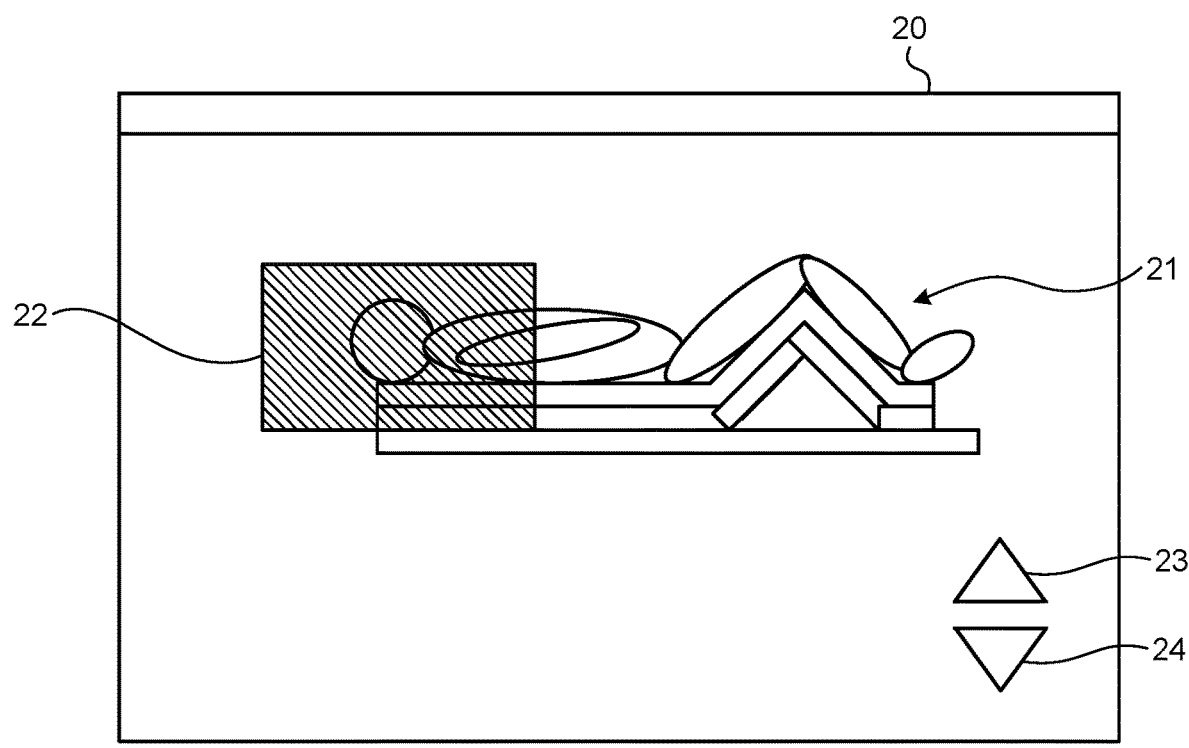
FIG. 9 is a view of an example graphical user interface (GUI) displayed by the couch control function according to the second embodiment.
Figure 10:
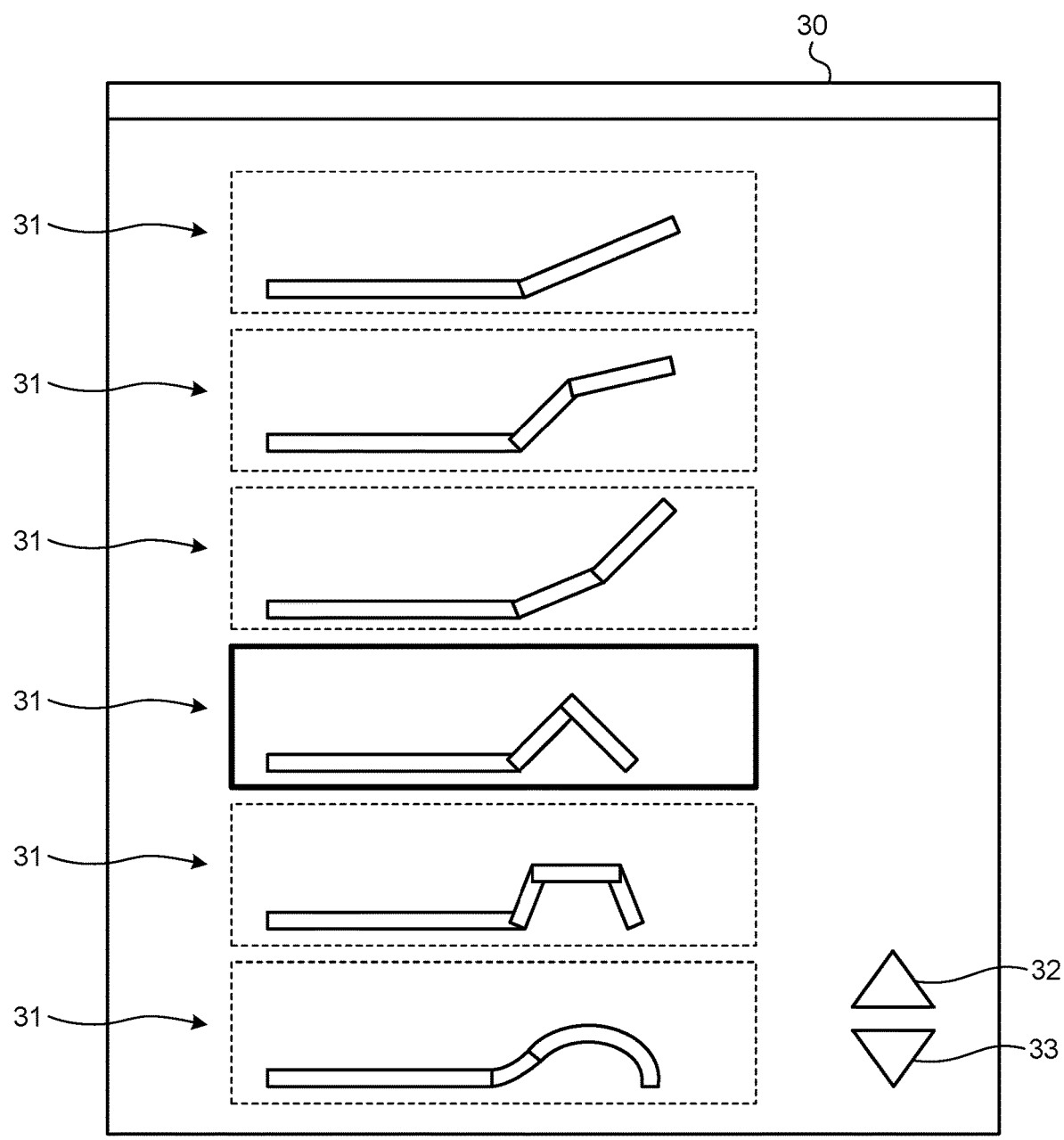
FIG. 10 is a view of an example GUI displayed by the couch control function according to the second embodiment.

FIGS. 9 and 10 are views of example graphical user interfaces (GUIs) displayed by the couch control function 14a according to the second embodiment.

For example, as illustrated in FIG. 9, the couch control function 14a displays, in a display region 20 of an information display terminal including a touch panel, a pictorial FIG. 21 indicating a state of the subject S and the couchtop 9a, and a pictorial FIG. 22 indicating a range of a bending restricted region. The couch control function 14a further displays, in the display region 20, a pictorial FIG. 23 indicating a button used to instruct the bendable couchtop 9d to bend greater, and a pictorial FIG. 24 indicating a button used to instruct the bendable couchtop 9d to bend smaller.

The couch control function 14a then accepts, from the operator, an operation of pressing down any one of the pictorial FIGS. 23 and 24 indicating the two buttons, follows the accepted operation, and causes the bendable couchtop 9d to bend.

As another example, for example, the couch control function 14a may display information indicating a shape when the bendable couchtop 9d is caused to bend within a range excluding a bending restricted region, and may accept, from the operator, an instruction of causing the bendable couchtop 9d to bend. In this case, for example, the couch control function 14a displays information indicating a plurality of shapes, as candidates, when the bendable couchtop 9d is caused to bend within the range excluding the bending restricted region, and causes the bendable couchtop 9d to bend into a shape selected by the operator from among the shapes.

For example, as illustrated in FIG. 10, the couch control function 14a displays, in a display region 30 of the information display terminal including the touch panel, pictorial FIG. 31 indicating a plurality of different shapes when the bendable couchtop 9d is caused to bend within the range excluding the bending restricted region. The couch control function 14a further displays, in the display region 20, a pictorial FIG. 32 indicating a button used to instruct the bendable couchtop 9d to bend greater, and a pictorial FIG. 33 indicating a button used to instruct the bendable couchtop 9d to bend smaller.

At this time, for example, the couch control function 14a determines, based on the number and the shape of the plate members 9f configuring the bendable couchtop 9d, for example, a plurality of shapes that are possible to form when the bendable couchtop 9d is caused to bend within the range excluding the bending restricted region. For example, the couch control function 14a may use a learned model created through machine learning to determine a plurality of shapes for the bendable couchtop 9d. Here, for example, the learned model is created beforehand through machine learning based on, as learning data, type information and position information of the local coil 5, and shapes for the bendable couchtop 9d, which are possible to form when a bending restricted region is set based on the type information and the position information. The learned model is then stored in the storage 13. In this case, the learned model is a model that accepts type information and position information of the local coil 5, and outputs at least one shape for the bendable couchtop 9d.

The couch control function 14a then accepts, from the operator, an operation of selecting one pictorial FIG. 31 from among the pictorial FIG. 31 indicating the shapes for the bendable couchtop 9d, and an operation of pressing down any one of the pictorial FIGS. 32 and 33 indicating the two buttons, follows the accepted operation, and causes the bendable couchtop 9d to bend to achieve the shape corresponding to the selected pictorial FIG. 31.

As described above, in the second embodiment, the couch control function 14a presents, to the operator, information indicating a range of a bending restricted region set for the bendable couchtop 9d, and accepts, from the operator, an instruction of causing the bendable couchtop 9d to bend within a range excluding the bending restricted region. In the second embodiment, the couch control function 14a further displays information indicating shapes when the bendable couchtop 9d is caused to bend within the range excluding the bending restricted region, and accepts, from the operator, an instruction of causing the bendable couchtop 9d to bend.

According to such a configuration as described above, the operator is able to intuitively know shapes when the bendable couchtop 9d is caused to bend. Therefore, according to the second embodiment, a subject and a technician, for example, are able to more easily provide an instruction of causing the bendable couchtop 9d to bend.

Third Embodiment

For example, in the first embodiment described above, the example case has been described where the local coil 5 is used as a receiver coil. There are embodiments that are not limited by the example case, however. For example, even when the WB coil 4 is used as a receiver coil, a similar embodiment is applicable. Such an example case will now be described as a third embodiment.

Figure 11:
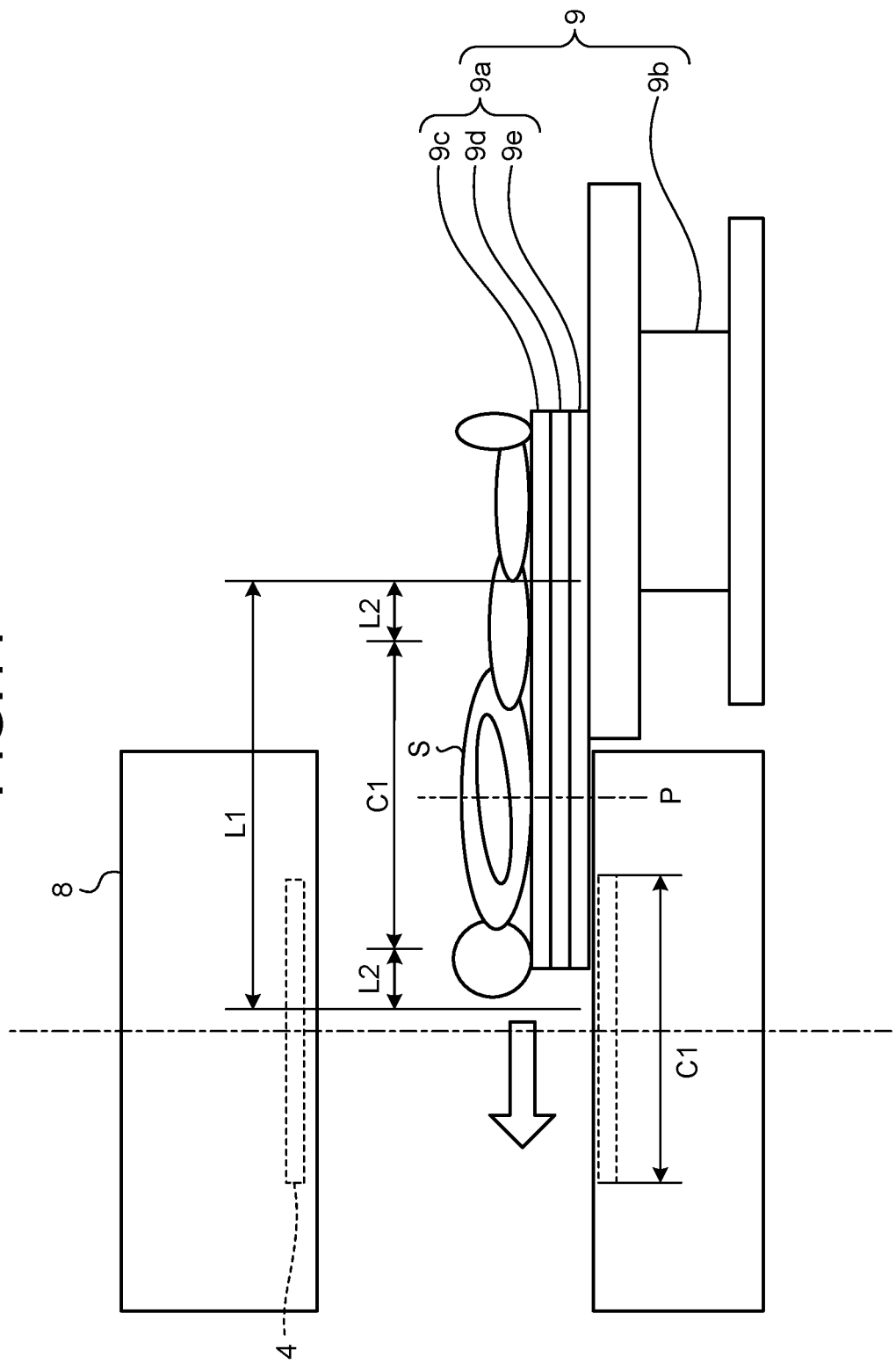
FIG. 11 is a view of an example of how a couch control function according to a third embodiment sets a transformation controlled region.

FIG. 11 is a view of an example of how the couch control function 14a according to the third embodiment sets a transformation controlled region.

For example, as illustrated in FIG. 11, when the WB coil 4 is used as a receiver coil, the couch control function 14a sets, as the bending restricted region L1, a range within which the additional regions L2 are added at positions in front of and behind a region having a size identical to a coil length Cl of the WB coil 4.

In this case, for example, the couch control function 14a determines, when a position P that is regarded as the center of a magnetic field on the couchtop 9a is determined, whether the WB coil 4 is used as a receiver coil, based on an imaging-target portion that imaging conditions entered by the operator includes, for example. For example, the determination referred herein of the position P on the couchtop 9a takes place, before the subject S is moved into the bore 8a, with a method using a light projector provided to the gantry 8, for example. The couch control function 14a then acquires, when it is determined that the WB coil 4 is used as a receiver coil, the coil length Cl of the WB coil 4, which is stored beforehand in the storage 13, as type information. The couch control function 14a further acquires information indicating the position P that is regarded as the center of the magnetic field on the couchtop 9a, as position information of the WB coil 4.

After that, the couch control function 14a sets, based on the acquired type information and the acquired position information, a bending restricted region for the bendable couchtop 9d. Specifically, the couch control function 14a sets, as the bending restricted region, a range within which the additional regions L2 are added, in the advancing direction of the bendable couchtop 9d, at positions in front of and behind a region having a size identical to the coil length Cl of the WB coil 4. Here, the method of setting the bending restricted region L1 and the additional regions L2 is similar to the method according to the first embodiment described above.

As described above, according to the third embodiment, when the WB coil 4 is used as a receiver coil, setting a bending restricted region based on the WB coil 4 makes it possible to restrict the bendable couchtop from bending at a position adjacent to an imaging-target portion, which may affect image quality, and to suppress image quality from lowering due to a body movement of the subject S. Furthermore, on the other hand, causing the bendable couchtop to bend within a range excluding the bending restricted region allows the subject S to secure a comfortable posture without using a cushion, for example. Therefore, according to the third embodiment, it is also possible to reduce a burden on a subject and a technician, for example, involving suppression of body movements of the subject.

Other Embodiments

As other embodiments, for example, the couch control function 14a may further present information to be referred to when the operator provides an instruction of causing the bendable couchtop 9d to bend. In this case, for example, the couch control function 14a presents reference information to the operator via an output device such as a display or a loudspeaker.

For example, the couch control function 14a identifies, based on disease information, contraindication information, and other information that patient information includes, when the patient information regarding the subject S has been acquired, a portion that tends to move unintentionally, a portion that easily moves, a portion that does not cause any problems to arise if it moves, and other portions of the subject S, and presents information regarding the identified portions as reference information.

For example, the couch control function 14a may cause, each time imaging takes place, the storage 13 to store information indicating a shape of the bendable couchtop 9d during the imaging and the identification information regarding the subject S in such a manner that the information and the identification information are associated with each other. The couch control function 14a may then present, when the identical subject S undergoes imaging for the second time and onward, the information indicating the shape of the bendable couchtop 9d, which was taken during the previous imaging, as reference information. For example, the couch control function 14a may display, when information indicating shapes for the bendable couchtop 9d is caused to display with GUIs, as described in the second embodiment, the shape taken during the previous imaging. For example, the couch control function 14a may display, in a highlighted manner, when information indicating a plurality of shapes for the bendable couchtop 9d is caused to display as a plurality of candidates with GUIs, as described in the second embodiment, the shape taken during the previous imaging, among the candidates.

In the embodiments described above, the example cases have been described where the couch controller in the present specification is achieved by the couch control function 14a of the processing circuitry 14. There are embodiments that are not limited by the example cases, however. For example, the couch controller in the present specification may be achieved with the couch control function 14a described in the embodiments. The function may otherwise be implemented with only hardware, only software, or a combination of hardware and software.

The term "processor" described above means, for example, circuitry including a central processing unit (CPU), a graphics processing unit (GPU), an application specific integrated circuit (ASIC), and a programmable logic device (e.g., a simple programmable logic device (SPLD), a complex programmable logic device (CPLD), and a field programmable gate array (FPGA)). When the processor is a CPU, for example, the processor reads and executes the computer programs stored in the storage to achieve the functions. By contrast, when the processor is an ASIC, for example, the functions are directly embedded as logic circuitry in circuitry in the processor, instead of storing the computer programs in the storage. The processors according to the present embodiments are not limited to those where each of the processors is configured as single circuitry. A plurality of independent circuitries, however, may be combined to configure a single processor to achieve the functions. Furthermore, the components in FIG. 1 may be integrated into a single processor to achieve the functions.

Here, the computer programs that the processor executes are provided in such a manner that the computer programs are stored in a non-transitory storage medium, for example. For example, the computer programs are provided in such a manner that the computer programs are incorporated beforehand in a storage such as a read only memory (ROM). For example, the computer programs may otherwise be provided in such a manner that the computer programs in the form of files in a format installable to a storage or in an executable format are recorded in a computer-readable storage medium such as compact disc read only memory (CD-ROM), a flexible disc (FD), a compact disc recordable (CD-R), or a digital versatile disc (DVD). The computer programs may be stored on a computer connected to a network such as the Internet, downloaded via the network, and provided or distributed. For example, the computer programs each include modules serving as functional units as described above. In actual hardware, as a CPU reads, from a storage medium such as a ROM, and executes each of the computer programs, the modules are loaded on a main storage device, and then generated on the main storage device.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging device, comprising:
a couch including:
  a transformable couchtop configured to be at least partially transformable and to support a subject, and
  a movement mechanism configured to cause the transformable couchtop to move into a gantry of the magnetic resonance imaging device,
wherein the couch further includes a movable couchtop configured to support the transformable couchtop in a transformable manner and to be movable in a direction toward the gantry, and the movement mechanism is configured to move the movable couchtop in the direction toward the gantry and thereby cause the transformable couchtop to move into the gantry; and
processing circuitry configured to:
  acquire information regarding a receiver coil used in imaging of the subject, and
  control transformation of the transformable couchtop based on the information regarding the receiver coil.

2. The magnetic resonance imaging device according to claim 1, wherein the processing circuitry is further configured to acquire, as the information regarding the receiver coil, type information and position information of the receiver coil.

3. The magnetic resonance imaging device according to claim 2, wherein the processing circuitry is further configured to acquire, as the type information, a coil length of the receiver coil, and information indicating an imaging-target portion of the receiver coil.

4. The magnetic resonance imaging device according to claim 1, wherein the processing circuitry is further configured to set, based on the information regarding the receiver coil, a transformation controlled region within which the transformation of the transformable couchtop is controlled.

5. The magnetic resonance imaging device according to claim 4, wherein the processing circuitry is further configured to set the transformation controlled region when the receiver coil is connected to the couch.

6. The magnetic resonance imaging device according to claim 1, wherein the transformation includes bending.

7. The magnetic resonance imaging device according to claim 1, wherein the receiver coil has a function of receiving a magnetic resonance signal generated from the subject.

8. The magnetic resonance imaging device according to claim 7, wherein the receiver coil further has a function of applying a high-frequency magnetic field to the subject.

9. A magnetic resonance imaging device, comprising:
a couch including
  a transformable couchtop configured to be at least partially transformable and to support a subject, and
  a movement mechanism configured to cause the transformable couchtop to move into a gantry of the magnetic resonance imaging device; and
processing circuitry configured to
  acquire information regarding a receiver coil used in imaging of the subject, and
  control transformation of the transformable couchtop based on the information regarding the receiver coil, wherein
the processing circuitry is further configured to acquire, as the information regarding the receiver coil, type information and position information of the receiver coil, and
the processing circuitry is further configured to acquire, as the position information, a range within which the receiver coil is allowed to be disposed.

10. The magnetic resonance imaging device according to claim 9, wherein the processing circuitry is further configured to acquire, based on a cable length of a cable attached to the receiver coil, the range within which the receiver coil is allowed to be disposed.

11. The magnetic resonance imaging device according to claim 9, wherein the processing circuitry is further configured to use a learned model constructed through machine learning using, as learning data, disposed positions of the receiver coil in past examinations to estimate the range within which the receiver coil is allowed to be disposed.

12. A magnetic resonance imaging device, comprising:
a couch including
  a transformable couchtop configured to be at least partially transformable and to support a subject, and
  a movement mechanism configured to cause the transformable couchtop to move into a gantry of the magnetic resonance imaging device; and
processing circuitry configured to
  acquire information regarding a receiver coil used in imaging of the subject, and
  control transformation of the transformable couchtop based on the information regarding the receiver coil, wherein
the processing circuitry is further configured to set, based on the information regarding the receiver coil, a transformation controlled region within which the transformation of the transformable couchtop is controlled, and
the transformation controlled region is determined so that a ratio of a length of the transformation controlled region with respect to a coil length of the receiver coil becomes a predetermined value.

13. The magnetic resonance imaging device according to claim 12, wherein the ratio is 1.0 or greater.

14. A magnetic resonance imaging device, comprising:
a couch including
  a transformable couchtop configured to be at least partially transformable and to support a subject, and
  a movement mechanism configured to cause the transformable couchtop to move into a gantry of the magnetic resonance imaging device; and processing circuitry configured to
acquire information regarding a receiver coil used in imaging of the subject, and
control transformation of the transformable couchtop based on the information regarding the receiver coil, wherein
the processing circuitry is further configured to set, based on the information regarding the receiver coil, a transformation controlled region within which the transformation of the transformable couchtop is controlled, and
the processing circuitry is further configured to set, as the transformation controlled region, a range within which additional regions are added, in an advancing direction of the transformable couchtop, at positions in front of and behind a region determined based on a coil length of the receiver coil.

15. The magnetic resonance imaging device according to claim 14, wherein the processing circuitry is further configured to acquire patient information regarding the subject, and to set, when the subject is determined to have claustrophobia based on the patient information, the additional regions having smaller sizes, compared with a case where the subject is determined not to have claustrophobia, so as to moderate restrictions to movements of the subject.

16. A magnetic resonance imaging device, comprising:
a couch including
a transformable couchtop configured to be at least partially transformable and to support a subject, and
a movement mechanism configured to cause the transformable couchtop to move into a gantry of the magnetic resonance imaging device; and
processing circuitry configured to
acquire information regarding a receiver coil used in imaging of the subject, and
control transformation of the transformable couchtop based on the information regarding the receiver coil, wherein
the processing circuitry is further configured to set, based on the information regarding the receiver coil, a transformation controlled region within which the transformation of the transformable couchtop is controlled, and
the processing circuitry is further configured to present, to an operator, information indicating a range of the transformation controlled region set for the transformable couchtop, and to accept, from the operator, an instruction of causing the transformable couchtop to be transformed within a range excluding the transformation controlled region.

17. A couch for a magnetic resonance imaging device, the couch comprising:
a transformable couchtop configured to be at least partially transformable and to support a subject;
a movement mechanism configured to cause the transformable couchtop to move into a gantry of the magnetic resonance imaging device; and
processing circuitry configured to
acquire information regarding a receiver coil used in imaging of the subject, and
control transformation of the transformable couchtop based on the information regarding the receiver coil,
wherein the couch further includes a movable couchtop configured to support the transformable couchtop in a transformable manner and to be movable in a direction toward the gantry, and
the movement mechanism is configured to move the movable couchtop in the direction toward the gantry and thereby cause the transformable couchtop to move into the gantry.

* * * * *